(12) United States Patent
Estes et al.

(10) Patent No.: US 8,786,856 B2
(45) Date of Patent: Jul. 22, 2014

(54) METHOD AND APPARATUS FOR MONITORING COMBUSTION PROPERTIES IN AN INTERIOR OF A BOILER

(75) Inventors: Michael John Estes, Longmont, CO (US); Andrew D. Sappey, Lakewood, CO (US); Henrik Hofvander, Boulder, CO (US); Allen Molitoris, Westminster, CO (US); Bernard Patrick Masterson, Louisville, CO (US); Pei Huang, Lafayette, CO (US)

(73) Assignee: Zolo Technologies, Inc., Boulder, CO (US)

( * ) Notice: Subject to any disclaimer, the term of this patent is extended or adjusted under 35 U.S.C. 154(b) by 634 days.

(21) Appl. No.: 13/142,791

(22) PCT Filed: Jan. 7, 2010

(86) PCT No.: PCT/US2010/020345
§ 371 (c)(1),
(2), (4) Date: Aug. 26, 2011

(87) PCT Pub. No.: WO2010/080892
PCT Pub. Date: Jul. 15, 2010

(65) Prior Publication Data
US 2011/0300492 A1    Dec. 8, 2011

Related U.S. Application Data

(60) Provisional application No. 61/143,732, filed on Jan. 9, 2009, provisional application No. 61/144,384, filed on Jan. 13, 2009.

(51) Int. Cl.
*G01B 11/00* (2006.01)
*F23N 5/08* (2006.01)
*G01B 11/27* (2006.01)
*G01N 21/84* (2006.01)
*G01N 21/39* (2006.01)
*F23M 5/08* (2006.01)

(52) U.S. Cl.
CPC ............... *G01N 21/84* (2013.01); *F23N 5/082* (2013.01); *G01B 11/27* (2013.01); *G01N 21/39* (2013.01); *F23M 5/08* (2013.01)
USPC ........ 356/399; 356/400; 356/401; 356/239.2; 250/554; 122/510; 122/6 A; 431/2

(58) Field of Classification Search
CPC ........ G01B 11/27; G01B 11/272; G03F 9/70; G03F 7/70358; H01L 21/681; F23N 5/08; G01N 21/00
USPC ............... 356/399–401, 239.2; 122/510, 6 A; 431/12; 250/554
See application file for complete search history.

(56) References Cited

U.S. PATENT DOCUMENTS

| | | | |
|---|---|---|---|
| 2,841,122 A * | 7/1958 | Tollow | 122/6 A |
| 3,754,533 A * | 8/1973 | Franzmann et al. | 122/510 |
| 4,011,403 A | 3/1977 | Epstein et al. | |
| 4,028,081 A | 6/1977 | Marcatili | |
| 4,037,113 A | 7/1977 | Moore | |
| 4,305,640 A | 12/1981 | Cullis et al. | |
| 4,360,372 A | 11/1982 | Maciejko | |
| 4,432,286 A | 2/1984 | Witte | |
| 4,672,198 A | 6/1987 | Presby | |
| 4,895,421 A | 1/1990 | Kim et al. | |
| 4,915,468 A | 4/1990 | Kim et al. | |
| 4,989,979 A | 2/1991 | Buckman | |
| 5,042,905 A | 8/1991 | Anjan et al. | |
| 5,068,515 A | 11/1991 | Van den Bergh et al. | |
| 5,291,013 A | 3/1994 | Nafarrate et al. | |
| 5,317,165 A | 5/1994 | Montagna | |
| 5,396,506 A | 3/1995 | Ball | |
| 5,418,881 A | 5/1995 | Hart, Jr. et al. | |
| 5,436,444 A | 7/1995 | Rawson | |
| 5,448,071 A | 9/1995 | Mccaul et al. | |
| 5,468,239 A | 11/1995 | Tanner et al. | |
| 5,477,323 A | 12/1995 | Andrews et al. | |
| 5,506,721 A | 4/1996 | Hikami et al. | |
| 5,553,179 A | 9/1996 | Cryan et al. | |
| 5,592,217 A | 1/1997 | Hirvonen | |
| 5,598,264 A | 1/1997 | Failes | |
| 5,621,213 A | 4/1997 | Barshad | |
| 5,701,376 A | 12/1997 | Shirasaki | |
| 5,717,450 A | 2/1998 | Hutt et al. | |

| | | | | | | |
|---|---|---|---|---|---|---|
| 5,732,166 | A | 3/1998 | Hamann et al. | JP | 2004-117236 | 4/2004 |
| 5,742,715 | A | 4/1998 | Boehlke et al. | JP | 2004-354671 A | 12/2004 |
| 5,798,840 | A | 8/1998 | Beiting | JP | 2006-522938 | 10/2006 |
| 5,802,222 | A | 9/1998 | Rasch et al. | WO | WO 2004/090496 A2 | 10/2004 |
| 5,805,318 | A | 9/1998 | Rabinovich et al. | | | |
| 5,813,767 | A | 9/1998 | Calabro et al. | | | |
| 5,841,915 | A | 11/1998 | Rabinovich et al. | | | |
| 5,930,029 | A | 7/1999 | Mehuys | | | |
| 5,933,000 | A | 8/1999 | Bosselmann et al. | | | |
| 5,960,129 | A | 9/1999 | Kleinschmitt | | | |
| 6,016,372 | A | 1/2000 | Fein et al. | | | |
| 6,018,413 | A | 1/2000 | Oka | | | |
| 6,042,365 | A | 3/2000 | Chen | | | |
| 6,064,417 | A | 5/2000 | Harrigan et al. | | | |
| 6,124,597 | A | 9/2000 | Shehada et al. | | | |
| 6,148,131 | A | 11/2000 | Geertman | | | |
| 6,150,661 | A | 11/2000 | Mccaul et al. | | | |
| 6,160,255 | A | 12/2000 | Sausa | | | |
| 6,169,830 | B1 | 1/2001 | Kewitsch et al. | | | |
| 6,297,504 | B1 | 10/2001 | Andreou | | | |
| 6,345,134 | B1 | 2/2002 | Laming et al. | | | |
| 6,351,587 | B1 | 2/2002 | Holland | | | |
| 6,363,190 | B1 | 3/2002 | Chen | | | |
| 6,366,355 | B1 | 4/2002 | Degroot | | | |
| 6,385,372 | B1 | 5/2002 | Yang | | | |
| 6,396,056 | B1 | 5/2002 | Lord | | | |
| 6,434,302 | B1 | 8/2002 | Fidric et al. | | | |
| 6,455,851 | B1 | 9/2002 | Lord et al. | | | |
| 6,469,785 | B1 | 10/2002 | Duveneck et al. | | | |
| 6,510,265 | B1 | 1/2003 | Giaretta et al. | | | |
| 6,519,385 | B1 | 2/2003 | Green | | | |
| 6,542,679 | B2 | 4/2003 | DiGiovanni et al. | | | |
| 6,593,573 | B1 | 7/2003 | Mccann et al. | | | |
| 6,678,451 | B2 | 1/2004 | Kim et al. | | | |
| 6,701,753 | B2 | 3/2004 | Dong et al. | | | |
| 6,766,070 | B2 | 7/2004 | Williams et al. | | | |
| 6,791,689 | B1 | 9/2004 | Weckstrom | | | |
| 6,903,822 | B2 | 6/2005 | Kakuho et al. | | | |
| 7,158,552 | B2 | 1/2007 | Buchold et al. | | | |
| 7,248,755 | B2 | 7/2007 | Sappey et al. | | | |
| 7,469,092 | B2 * | 12/2008 | Sappey et al. ........... 385/147 | | | |
| 8,544,279 | B2 * | 10/2013 | Sappey et al. ........... 60/772 | | | |
| 2001/0035952 | A1 * | 11/2001 | Merklein ............ 356/239.2 | | | |
| 2002/0031737 | A1 | 3/2002 | Von Drasek et al. | | | |
| 2002/0158202 | A1 | 10/2002 | Webber et al. | | | |
| 2002/0181856 | A1 | 12/2002 | Sappey et al. | | | |
| 2003/0026541 | A1 | 2/2003 | Sappey et al. | | | |
| 2003/0067952 | A1 | 4/2003 | Tsukiji et al. | | | |
| 2003/0101774 | A1 | 6/2003 | Oh et al. | | | |
| 2003/0191397 | A1 | 10/2003 | Webb | | | |
| 2004/0008744 | A1 | 1/2004 | Okazaki et al. | | | |
| 2004/0101305 | A1 | 5/2004 | Jung et al. | | | |
| 2004/0160596 | A1 | 8/2004 | He et al. | | | |
| 2006/0147166 | A1 | 7/2006 | Roba et al. | | | |
| 2006/0278240 | A1 | 12/2006 | Spillman et al. | | | |
| 2007/0217744 | A1 | 9/2007 | Debut et al. | | | |
| 2008/0002186 | A1 | 1/2008 | Masterson et al. | | | |
| 2008/0074645 | A1 | 3/2008 | Sappey | | | |
| 2009/0080054 | A1 | 3/2009 | Koyata et al. | | | |
| 2011/0188039 | A1 | 8/2011 | Aoyama | | | |
| 2012/0025112 | A1 | 2/2012 | Li | | | |

FOREIGN PATENT DOCUMENTS

| | | |
|---|---|---|
| CN | 1163665 A | 10/1997 |
| CN | 1343873 | 4/2002 |
| EP | 766080 | 4/1997 |
| GB | 2127174 A | 4/1984 |
| JP | 63-133035 | 6/1988 |
| JP | 04-251214 | 9/1992 |
| JP | 07-504828 | 6/1995 |
| JP | 09-073020 | 3/1997 |
| JP | 09-152126 | 6/1997 |
| JP | 10-301153 | 11/1998 |
| JP | 2000-074830 | 3/2000 |
| JP | 2000-121558 | 4/2000 |
| JP | 2001-215343 | 8/2001 |
| JP | 2002-236227 | 8/2002 |
| JP | 2003-084324 | 3/2003 |

OTHER PUBLICATIONS

International Search Report and Written Opinion from PCT/US05/02853, dated Aug. 29, 2005.

Severin et al. (1989) "Bandwith and Modal Noise Effects in Fused-Head-End Multimode Fiber Passive Components" Journal of Lightwave Technology, vol. 7, No. 12, pp. 11-19.

Supplemental European Search Report for Application No. EP 10729501.6, mailed on Nov. 27, 2013.

International Preliminary Report on Patentability, Written Opinon and International Search Report from PCT/US2010/020345, dated Jul. 21, 2011 and Jun. 29, 2010.

International Search Report and Written Opinion from PCT/US13/032479, dated Jun. 28, 2013.

Allen (1998) "Diode laser absorption sensor for gas-dynamic and combustion flows" Measuring Science and Technology 9:545.

Allen et al. (2002) "Tunable Diode Laser Sensing and Combustion Control" Applied Combustion Diagnostics, chapter 18.

Baer et al. (1994) "Multiplexed Diode-Laser Sensor System for Simultaneous H20, O2, and Temperature Measurements" Optics Letters (19)22:1900-1902.

Docquier and Candel (2002) "Combustion control and sensors: a review" Progress and Energy and Combustion Science 28, 107-150.

Ebert et al. (1998) "Simultaneous Laser-Based in situ Detection of Oxygen and Water in a Waster Incinerator for Active Combustion Control Purposes" 27th Symposium on Combustion pp. 1301-1308.

Ebert et al. (2000) "Simultaneous Diode-Laser-Based In Situ Detection of Multiple Species and Temperature in a Gas-Fired Power Plant" Proceedings of the Combustion Institute 28.423.

Ebert et al. (2000) "The Use of Lasers as the Basis for Combustion Equipment Control" at TOTem, Intelligent Combustion Control pp. 1-15.

Englsh translation of a Japanese Office action received Apr. 8, 2010 for corresponding JP Application No. 2007-506152.

English translation of a Chinese Office action received Mar. 25, 2010 for corresponding CN Application No. 200580010448.0.

Furlong et al. (1998) "Diode Laser Sensors for Real-Time Control of Pulsed Combustion Systems"; AIAA/SAE/ASME/ASEE Joint Propulsion Conference and Exhibit, pp. 1-8, 1.XP001148178.

Furlong et al. (1998) "Real-Time Adaptive Combustion Control Using Diode-Laser Absorption Sensors," 27th Symposium on Combustion pp. 103-111.

Liu et al. (2003) "Diode Laser Absorption Diagnostics for Measurements in Practical Combustion Flow Fields" 39th AIAA/ASME/SAE/ASEE Joint Propulsion Conference and Exhibit, Paper No. AIAA-2003-4581 pp. 1-6.

Ouyang et al. (1992) "Tomographic Absorption Spectroscopy of Combustion Gases using Tunable Infared Diode Lasers," Paper No. 1637-20, SPIE Conference on Environmental and Process Monitoring Technologies, pp. 163-172.

Phillippe et al. (1993) "Laser diode wavelength-modulation spectroscopy for simultaneous measurement of temperature, pressure, and velocity in shock-heated oxygen flows" Applied Optics 32:6090.

Sanders et al. (2000) "Diode-Laser Sensor for Monitoring Multiple Combustion Parameters in Pulse Detonation Engines" Proceedings of the Combustion Institute 28:587.

Sanders et al. (2001) "Diode-laser absorption sensor for line-of-sight gas temperature distributions" Applied Optics 40:4404.

Teichert et al. (2003) "Simultaneous in situ masurement of CO H₂O, and gas temperatures in a full-sized coal-fired power plant by near-infrared diode lasers" Applied Optics 42:2043.

Upschulte et al. (1999) "Measurements of CO, CO₂, OH, and H₂O in room-temperature and combustion gases by used of a broadly current-tuned multisection InGaAsP diode laser" Applied Optics 38:1506.

Varghese et al. (1997) "Temperature and CO2 Concentration Profiles in Flames Measured by Laster Absorption Tomography," Paper 97-0317, AIAA 35th Aerospace Sciences Meeting, Reno, NV.

Villarreal et al. (2005) "Frequency Resolved Absorption Tomography with Tunable Diode Lasers," Applied Optics 44:6786-6795.

Webber et al. (2000) "In Situ Combustion Measurements of CO, $CO_2$, $H_2O$ and Temperature Using Diode Laser Absorption Sensors" Proceedings of the Combustion Institute 28:407.

Wolfrum (1998) "Lasers in Combustion: From Basic Theory to Practical Devices" 27th Symposium on Combustion pp. 1-41.

Miller et al. (1996) "Diode laser-based air mass flux sensor for subsonic aeropropulsion inlets" Applied Optics 35:4905.

International Search Report and Written Opinion for corresponding International Application No. PCT/US2010/020345 mailed Jun. 29, 2010.

* cited by examiner

*Primary Examiner* — Tarifur Chowdhury

*Assistant Examiner* — Isiaka Akanbi

(74) *Attorney, Agent, or Firm* — Swanson & Bratschun, L.L.C.

(57) ABSTRACT

A method of monitoring combustion properties in an interior of a boiler of the type having walls comprising a plurality of parallel steam tubes separated by a metal membrane. First and second penetrations are provided in the metal membrane between adjacent tubes on opposite sides of the boiler. A beam of light is projected through a pitch optic comprising a pitch collimating lens and a pitch relay lens, both residing outside the boiler interior. The pitch relay lens projects the beam through a penetration into the boiler interior. The beam of light is received with a catch optic substantially identical to the pitch optic residing outside the boiler interior. The strength of the collimated received beam of light is determined. At least one of the pitch collimating lens and the catch collimating lens may then be aligned to maximize the strength of the collimated received beam.

20 Claims, 5 Drawing Sheets

Figure 1:
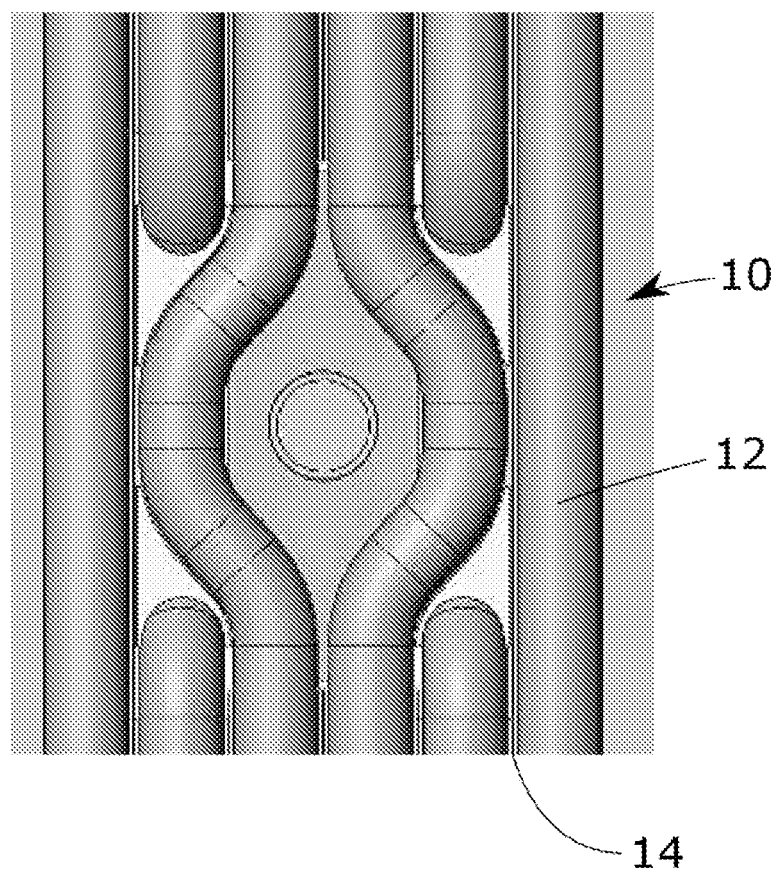

METHOD AND APPARATUS FOR MONITORING COMBUSTION PROPERTIES IN AN INTERIOR OF A BOILER

RELATED APPLICATIONS

This application is a 35 U.S.C. §371 national phase application of PCT/US10/20345 (WO 2010/080892), filed on Jan. 7, 2010, entitled "Method and Apparatus for Monitoring Combustion Properties in an Interior of a Boiler", which application claims the benefit of U.S. Provisional Application Ser. Nos. 61/144,384, filed Jan. 13, 2009 and 61/143,732, filed Jan. 9, 2009, each of which is incorporated herein by reference in its entirety.

TECHNICAL FIELD

The present disclosure is directed toward a method and apparatus for measuring combustion properties in an interior of a boiler, and more particularly toward a method and apparatus for measuring combustion properties in a boiler of the type having walls comprising a plurality of parallel steam tubes separated by a metal membrane without reconfiguring the steam tubes.

BACKGROUND

U.S. Pat. No. 7,469,092, entitled "Method and Apparatus For The Monitoring And Control Of A Process," describes a method and apparatus for the monitoring and control of a process using tunable diode laser absorption spectroscopy (TDLAS). Briefly stated, the TDLAS method and apparatus involves directing a beam of light, which may be a multiplexed beam of a number of distinct wavelengths, into a boiler combustion chamber to measure boiler combustion properties such as temperature and the concentration of various combustion species including $CO$, $CO_2$, $O_2$ and $H_2O$. The technique requires a line of sight through the boiler. In fact, many lines of sight are typically required as it is often desirable to measure combustion properties in multiple boiler locations. Typically a wavelength multiplexed laser beam is transmitted from a pitch optic to a catch optic on the opposite side of the boiler. Certain applications require up to 15 measurement paths, thus requiring 15 pitch/catch optic pairs and 30 boiler penetrations.

Typical coal-fire boilers comprise walls made of a series of parallel steam tubes spaced by a metal membrane. The steam tubes are typically about 2 inches (5.08 cm) in diameter and occur on about 2.5 inch (6.35 cm) centers. The metal membrane between the tubes is typically about 0.5 inch (1.27 cm) wide and 0.375 inch (0.9525 cm) thick. To gain optical access for measurements using a wavelength-multiplexed laser beam optical access must be provided through the wall of the boiler. Known TDLAS apparatus require an approximately 2 inch (5.08 cm) diameter hole in the boiler wall to provide adequate optical access.

FIG. 1 illustrates the current state of the art for providing optical access to a boiler interior. Referring to FIG. 1, the boiler wall 10 comprises a series of parallel steam tubes 12 separated by a metal membrane 14. To provide the required 2" hole for optical access, the tubes must be rerouted using tube bends as illustrated in FIG. 1. Once completed, the use of tube bends to provide the optical access works well. However, it is difficult and expensive to provide the required number of tube bends for satisfactory combustion monitoring. The problem stems primarily from the fact that in order to install even a single tube bend, the boiler must be shut down for a significant period of time. As a result, the tube bends and thus the TDLAS monitor can only be installed during a long planned outage. Planned outages occur only every one or two years. Thus, unfortunate timing may result in having to wait up to two years before a particular power plant will be in a position to purchase and install a TDLAS monitor. Thus, an apparatus for monitoring combustion properties within a boiler that eliminates the need for tube bends is highly desirable.

The present invention is directed toward overcoming one or more of the problems discussed above.

SUMMARY OF THE EMBODIMENTS

A first aspect of the disclosure is a method of monitoring combustion properties in an interior of a boiler of the type having walls comprising a plurality of parallel steam tubes separated by a metal membrane. The method comprises providing first and second penetrations in the metal membrane between adjacent tubes on opposite sides of the boiler without relocating the adjacent tubes. A beam of light is then projected through a pitch optic comprising a pitch collimating lens and a pitch relay lens, both residing outside the boiler interior. The pitch relay lens is optically coupled to the first penetration to project the beam into the boiler interior. The method further comprises receiving the beam of light with a catch optic residing outside the boiler interior. The catch optic comprises a catch relay lens optically coupled to the second penetration and a catch collimating lens optically coupled to the catch relay lens. The strength of the collimated received beam of light is determined. At least one of the pitch collimating lens and the catch collimating lens may then be aligned to maximize the strength of the collimated received beam. Embodiments may include both the pitch collimating lens and the catch collimating lens being aligned to maximize the strength of the received beam. The first and second penetrations may be elongated parallel to the steam tubes. The method may further comprise mounting the pitch optics in a pitch optics housing and the catch optics in a catch optics housing, with the pitch and catch relay lenses occupying an orifice in a leading wall of the pitch optics housing and the catch optics housing, respectively. In such an embodiment, the method may further comprise attaching proximal ends of first and second sight tubes to an exterior boiler wall with the first and second penetrations communicating with an interior of the first and second sight tubes, respectively. The pitch optics housing may be attached to the distal end of the first sight tube with the relay lens in optical communication with the interior of the first sight tube and the catch optics housing may be attached to the distal end of the second sight tube with the catch relay lens in optical communication with the interior of the second sight tube.

Another aspect of the disclosure is an apparatus for sensing combustion properties in an interior of a boiler, the boiler comprising a plurality of parallel steam tubes separated by a metal membrane. The apparatus comprises a diode laser having a select lasing frequency. A pitch collimating lens is optically coupled to a beam generating diode laser. A pitch relay lens is optically couple to the pitch collimating lens, with the pitch relay lens being configured to project the beam from the laser into a first penetration in a first membrane between adjacent tubes. A catch relay lens is configured to receive a projected beam through a second penetration in a second membrane substantially opposite the first membrane. A catch collimating lens is optically coupled to the catch relay lens and an optical fiber is optically coupled to the catch collimating lens. A detector sensitive to the select lasing frequency in turn is optically coupled to the optical fiber. An alignment mechanism is operatively associated with at least one of the pitch and catch collimating lenses to provide for alignment of the collimating lenses with respect to the beam to maximize the quantity of light received by the detector. The pitch collimating lens and pitch relay lens and the catch collimating lens and the catch relay lens may be contained within a pitch housing and a catch housing, respectively, as described above with regard to the first aspect. Embodiments may further include first and second sight tubes attached at their proximal ends to the boiler exterior with the penetrations communicating with the interior of the sight tubes. In such an embodiment the pitch housings and catch housings can be attached to the distal ends of the first and second sight tubes, respectively, with the relay lenses in optical communication with the interior of the sight tubes. Embodiments may include alignment mechanisms operatively associated with each of the pitch and catch collimating lenses. The alignment mechanism may comprise means to tilt the collimating lens along first and second orthogonal axis with both the first and second orthogonal axes being substantially orthogonal to the projection beam. A data processing system may be operatively associated with the detector and the alignment mechanism. The data processing system receives data from the detector and causes the alignment mechanisms to align the operatively associated collimating lenses to maximize the strength of the beam.

The method and apparatus for measuring combustion properties in an interior of a boiler described herein allows for detection of combustion properties without having to shut down the boiler to install tube bends to allow optical access. The method and apparatus therefore allow the many benefits of combustion monitoring to be enjoyed quickly and inexpensively as compared to systems requiring installation of tube bends.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

U.S. Pat. No. 7,469,092, the contents of which are hereby incorporated herein in their entirety, discloses a method and apparatus for monitoring and control of a combustion process of the type requiring installation of tube bends in the wall of a boiler in order to provide optical access to the boiler. U.S. Pat. No. 7,469,092 describes a sensing system which incorporates an auto-alignment feature that allows the pitch and catch optics to maintain optical alignment even though they are bolted onto a boiler or hostile process chamber which is, itself, subject to movement from thermal effects or wind and vibration.

Figure 2:
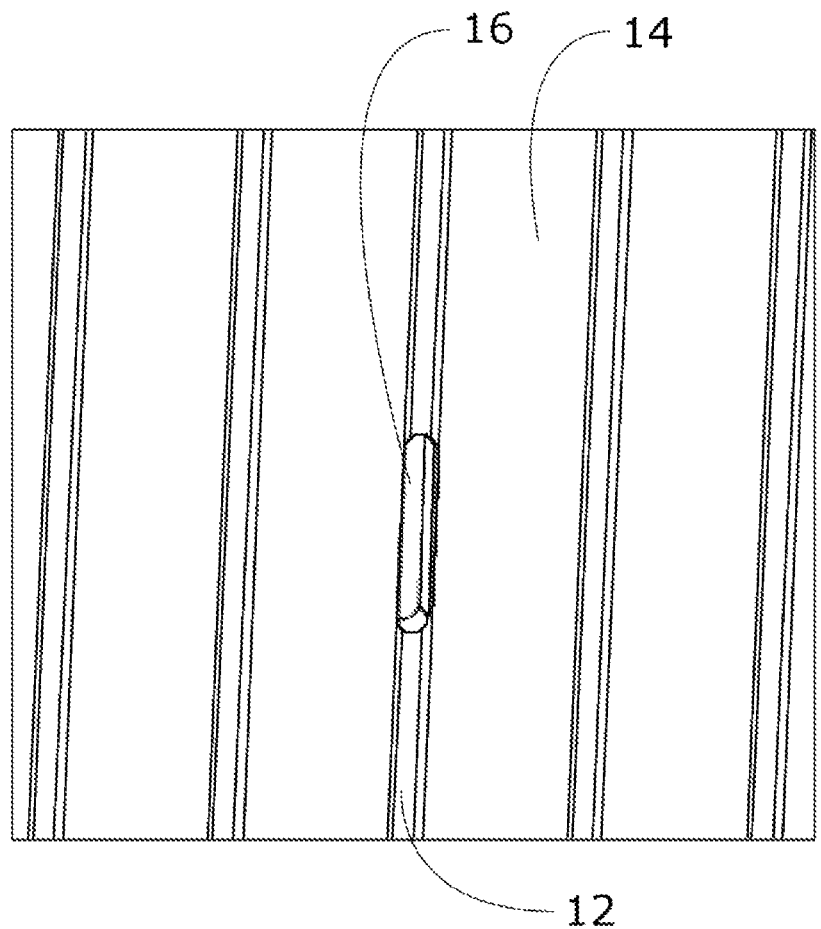

The described system provides pitch and catch optics including pitch and catch collimating lenses that are mounted on feedback-control tilt stages. Multiplexed light is launched across the measurement region by a collimating pitch lens attached directly to an input fiber and the catch collimating lens optically couples transmitted light to an output fiber that is typically a multi-mode fiber. As a result, the catch optic must be oriented so that it is collinear with the beam emanating from the pitch optic. This is necessary so that the focused transmitted beam will arrive within the acceptance cone of the multi-mode fiber. The system described in U.S. Pat. No. 7,469,092 contemplates a penetration in the wall of the boiler on the order of 2 inch (5.08 cm) in diameter. The described system functions with a 1 cm tolerance over a typical transmission distance of 10 meters, or 1 milliradian. However, this tolerance is not suitable if the boiler penetration is to be provided in the metal membrane between adjacent steam tubes to eliminate the need for providing tube bends. Such a penetration is illustrated in FIG. 2. The penetration 16 has approximately a ½ inch (1.27 cm) width (equal to the width of the membrane) and is elongate in a direction parallel to the steam pipes. Elongating the penetration in this way helps somewhat in terms of light collection efficiency. However, alignment and maintenance of alignment is significantly more difficult than required with a 2 inch (5.08 cm) penetration supported by the tube bend approach. By way of example, the lateral alignment tolerance, assuming a 15 meter wide boiler, is approximately 1.25 cm over 14 meters, or approximately 0.8 milliradians. In order to provide required alignment resolution, an alignment increment at least a factor of 10 smaller (i.e., 0.08 milliradians) is required. These tolerances cannot be achieved with the method and apparatus described in U.S. Pat. No. 7,469,092.

Figure 3:
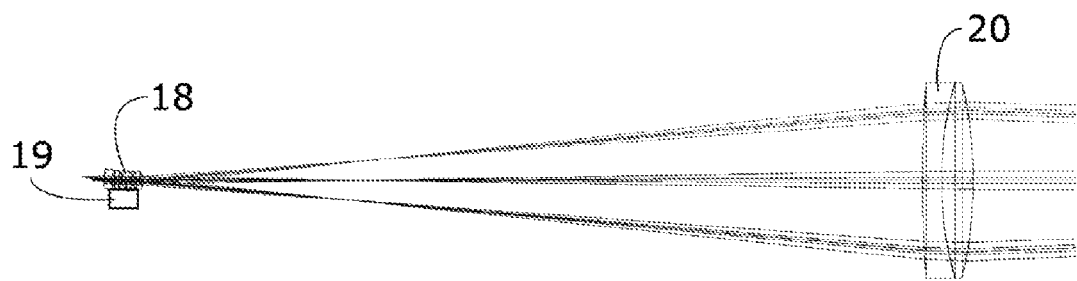
Figure 4:

To meet the tighter alignment tolerance, a modified pitch optic and catch optic configuration are required. Such a configuration is illustrated in FIGS. 3 and 4. The collimating lens 18 is mounted to a tilt stage 19 allowing it to be tilted along orthogonal 90° axes as described in greater detail below and in U.S. Pat. No. 7,469,092. Instead of directly launching the beam into the boiler from a collimating lens, a relay lens 20 is provided in optical communication with the collimating lens 18. The relay lens is aligned during construction on the axis of the slotted membrane penetration. As a result, the beam received by the relay lens must go through the slotted penetration 16 at what is the focal point of the relay lens. See FIG. 4. The angle that the beam goes through the slotted penetration can be adjusted in two dimensions by steering the beam from the collimating lens to different locations on the relay lens. This allows the beam to be steered through the slotted penetration at the pitch side to hit the slotted penetration, at the catch side of the boiler. On the catch side of the boiler, the catch optics incorporate a relay lens 20 and tilt collimating lens 18 in the same manner depicted in FIGS. 3 and 4. Use of the tilt stage on the catch collimating lens ensures a maximum strength collimated received beam is conveyed to an optically coupled multi-mode fiber. To further provide effective optical coupling, the pitch beam is collimated to a diameter of about 5 mm, as opposed to on the order of 20 mm in prior art systems.

Figure 5:
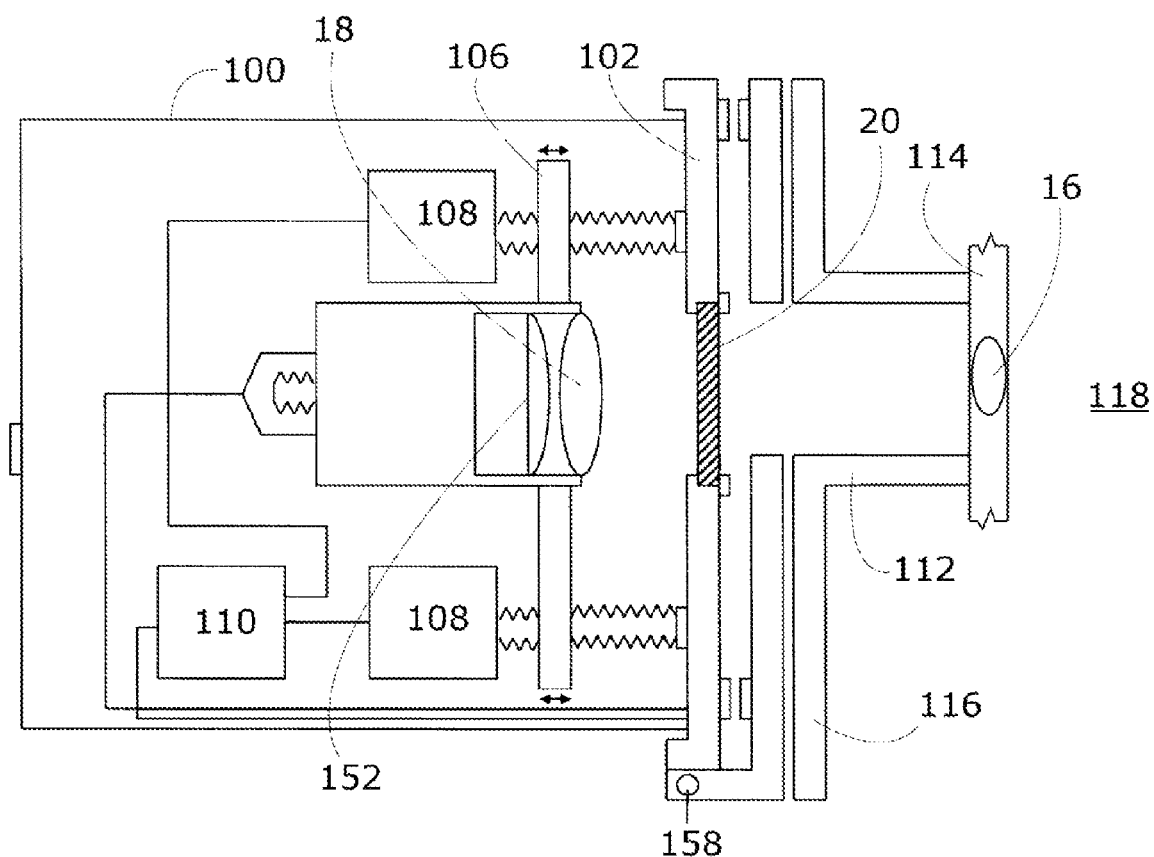

FIG. 5 schematically illustrates an embodiment of alignable pitch and catch optics. The transmitter and receiver are similar in design: the transmitter generates a collimated beam of laser light emerging from an optical fiber, and the receiver captures a collimated beam of light and focuses it into a fiber. (It is possible to send the light backward through this optical system, and most of the elements of the transmitter and receiver are identical.) The following description applies to either the transmitter or receiver module.

The pitch and catch optics may be mounted in a housing 100 with the leading side 102 having an orifice 104 occupied by relay lens 20. The housing may be an NEMA-4 enclosure to protect the pitch and catch optics from the environment. As shown in FIG. 5, a collimating lens 18 is attached to a kinematic tilt stage 106 positioned to tip and tilt the collimating lens 18 about orthogonal axes perpendicular to an optical axis of the pitch optics. Two direct drive stepper motors 108 accomplish the tip and tilt. These motors are controlled by a computer via an Ethernet or similar connection. This connection may be through an optical fiber in order to avoid electrical interference. The stepper motors 108 hold their positions when power is removed, so optical alignment is not effected by power outages. The stepper motors are driven by a motor drive 110.

During periodic or continuous system alignment, the control computer monitors the amount of laser light that is transmitted and detected. Preferably, a discrete alignment wavelength such as a visible or near-infrared light may be provided for continuous or periodic alignment proceedings. Any misalignment will reduce this detected signal. In auto-alignment mode, the computer measure the detected signal, directs one of the two stepper motors to move a small amount in one direction, then re-measures the detected signal. If the signal increases, the computer directs the stepper motor to move again in the same direction until the signal does not increase. The computer then directs the other stepper motor to move along the orthogonal axis to maximize the detected signal, then repeats the whole process for the other sensor head. As the detected signal increases, the detector amplifier gain automatically decreases so that the auto-alignment proceeds over several iterations of signal size. The auto-alignment system can function with detected powers from nanowatts to milliwatts.

This "hill-climbing" algorithm is able to align the system after near-total loss of signal, in the presence of substantial noise, and is tolerant of beam blockages, power outages, mechanical shocks and other disturbances that could cause other alignment systems to misalign to the limits of the control electronics. All that is required for auto alignment is a finite signal with a global maximum in position space. Depending on the specific installation conditions, auto-alignment may occur periodically at set intervals such as every hour or as needed after an extended period, such as days of operation. The control computer may monitor the directed signal and auto-align only when the signal drops below a preset threshold.

In one embodiment a sight tube 112 has a proximal and a distal end. The proximal end is attached to extend normally from an exterior wall 114 of the boiler with an elongate penetration 16 communicating with the interior of the sight tube 112. A flange 116 is provided at a distal end of the sight tube 112. The flange 116 allows the housing 100 to be attached with the leading end 102 abutting the boiler flange with the relay lens 20 in optical communication with the penetration 16. In this manner a beam may be transmitted into the boiler interior 118 through the penetration 16 and across the boiler to a receiver containing catch optics substantially identical to those described above with regard to FIG. 5.

Figure 6:
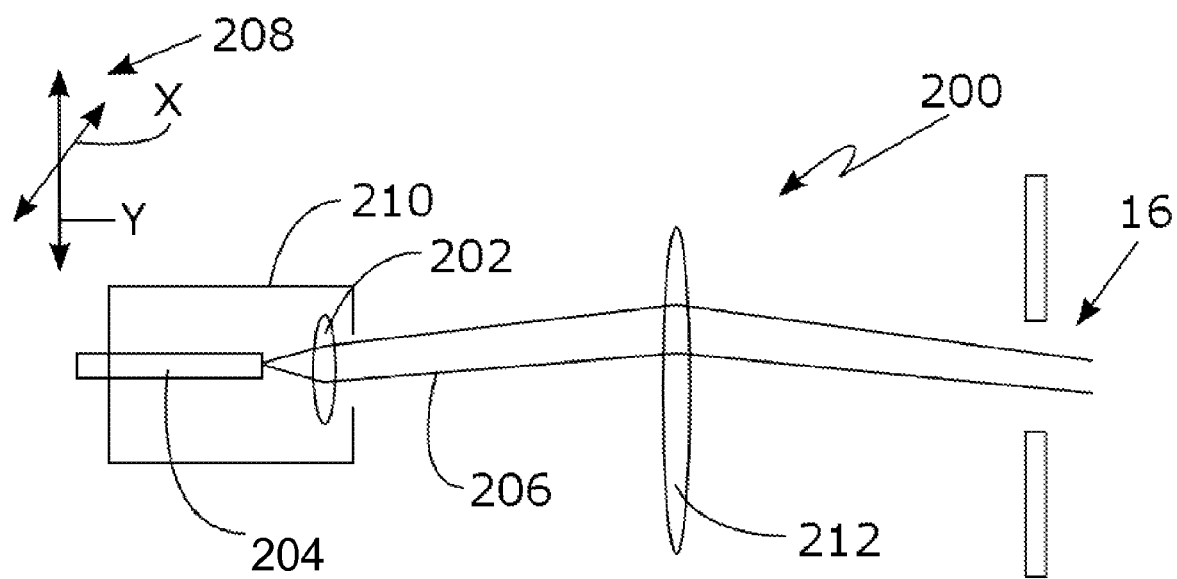

FIG. 6 illustrates an alternative embodiment of alignable pitch and catch optics 200. FIG. 6 will be described as a transmitter and a receiver is of similar design. In the alternative embodiment 200 a lens 202 is optically coupled to an optical fiber 204. The lens 202 is referred to herein as a "collimating" lens and may be a true collimating lens (that produces a beam of substantially constant diameter). Alternatively the collimating lens 202 may be a "near" collimating lens that provides a slight expansion of the beam 206. The fiber 204 and the lens 202 are mechanically linked together in a fixed relationship and movable by "translation" along orthogonal X-Y axes 208 by a translation mechanism 210. The emitted beam 206 is movable by translation to strike select portions of the relay lens 212 which directs the beam through the membrane slot and focuses the beam at about the receive or catch optic (corresponding to the lens 202 of the catch optic). Stepper motors, a computer controller and a "hill climbing" algorithm similar to that discussed above with respect to the embodiment of FIG. 5 are operatively associated with the translation mechanism 210 to provide for substantially continuous alignment correction.

Various embodiments of the disclosure could also include permutations of the various elements recited in the claims as if each dependent claim was multiple dependent claims incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method of monitoring combustion properties in an interior of a boiler of the type having walls comprising a plurality of parallel steam tubes separated by a metal membrane, the method comprises:
   a) providing first and second penetrations in the metal membrane between adjacent tubes on opposite sides of the boiler without relocating the adjacent tubes;
   b) projecting a beam of light through a pitch optic comprising a pitch collimating lens and a pitch relay lens both residing outside the boiler interior, the pitch relay lens being optically coupled to the first penetration to project the beam into the boiler interior and being configured to have a focal point at the first penetration;
   c) receiving the beam of light with a catch optic residing outside the boiler interior, the catch optic comprising a catch relay lens optically coupled to the second penetration and a catch collimating lens optically coupled to the catch relay lens;
   d) determining a strength of the collimated received beam of light; and
   e) aligning at least one of the pitch collimating lens and the catch collimating lens to maximize the strength of the collimated received beam.

2. The method of claim 1 wherein step e) further comprises aligning both the pitch collimating lens and the catch collimating lens to maximize the strength of the collimated received beam.

3. The method of claim 2 wherein step e) further comprises tilting the pitch and catch collimating lenses along first and second orthogonal axis.

4. The method of claim 3 wherein step e) further comprises sequentially tilting the pitch and catch optics to maximize the strength of the beam.

5. The method of claim 2 wherein step e) further comprises translating the pitch and catch optics along first and second orthogonal axes.

6. The method of claim 5 wherein step e) further comprises sequentially translating the pitch and catch optics to maximize the strength of the beam.

7. The method of claim 5 further comprising the pitch and catch collimating lenses being near collimating lenses.

8. The method of claim 1 wherein the first and second penetrations are elongated parallel to the steam tubes.

9. The method of claim 1 further comprising mounting the pitch optics in a pitch optics housing and the catch optics in a catch optics housing, with the pitch and catch relay lenses occupying an orifice in a leading wall of the pitch optics housing and the catch optics housing, respectively.

10. The method of claim 9 further comprising attaching a proximal end of first and second sight tubes to an exterior of the boiler with the first and second penetrations communicating with an interior of the first and second sight tubes, respectively.

11. The method of claim 10 further comprising attaching pitch optics housing and the catch optics housing to a distal end of the first and second sight tube, respectively, with the pitch relay lens and the catch relay lens adjacent the distal end of the first and second sight tubes, respectively.

12. An apparatus for sensing a combustion property in an interior of a boiler, the boiler comprising a plurality of parallel steam tubes separated by a metal membrane, the apparatus comprising:
   a diode laser having a select lasing frequency;
   a pitch collimating lens is optically coupled to a beam generated by the diode laser;
   a pitch relay lens is optically coupled to the pitch collimating lens, the pitch relay lens being configured to project the beam from the laser into a first penetration in a first membrane between adjacent tubes, with a focal point of the pitch relay lens being at the first penetration;
   a catch relay lens is configured to receive the projected beam through a second penetration in a second membrane substantially opposite the first membrane;
   a catch collimating lens optically coupled to the catch relay lens;
   an optical fiber optically coupled to the catch collimating lens;
   a detector sensitive to the select lasing frequency optically coupled to the optical fiber; and
   an alignment mechanism operatively associated with at least one of the pitch and catch collimating lenses to provide for alignment of the collimating lenses with respect to the beam to maximize a quantity of light received by the detector.

13. The apparatus of claim 12 further comprising a pitch housing containing the pitch collimating lens and pitch relay lens, with the pitch relay lens occupying an orifice in a leading wall of the pitch housing and a catch housing containing the catch collimating lens and the catch relay lens, with the catch relay lens occupying an orifice in a leading wall of the catch housing.

14. The apparatus of claim 13 further comprising first and second sight tubes, each having a proximal and a distal end, the proximal end of the first and second sight tubes being attached to an exterior of the boiler with the first and second penetrations communicating with an interior of the first and second sight tubes, respectively, and the pitch housing and the catch housing attached to the distal ends of the first and second sight tubes, respectively, with the respective pitch relay lens and catch relay lens in optical communication with the sight tube interiors.

15. The apparatus of claim 12 further comprising an alignment mechanism operatively associated with each of the pitch and catch collimating lenses.

16. The apparatus of claim 15 wherein each alignment mechanism comprises means to tilt the collimating lens along first and second orthogonal axes, with both the first and second orthogonal axes being substantially orthogonal to the projection beam.

17. The apparatus of claim 16 wherein the means to the tilt the collimating lens comprises a stepper motor.

18. The apparatus of claim 15 wherein each alignment mechanism comprises means to translate the collimating lens along first and second orthogonal axes.

19. The apparatus of claim 12 further comprising:
   a data processing system operatively associated with the detector and the alignment mechanism, the data processing system receiving data from the detector and further causing the alignment mechanism to align the operatively associated collimating lens to maximize the strength of the beam.

20. The apparatus of claim 19 wherein each collimating lens is a near collimating lens.

* * * * *